(12) United States Patent
Bonrath et al.

(10) Patent No.: US 7,169,943 B2
(45) Date of Patent: Jan. 30, 2007

(54) MANUFACTURE OF TOCOPHERYL ACETATE

(75) Inventors: Werner Bonrath, Freiburg (DE); Claus Dittel, Solothurn (CH); Thomas Netscher, Bad Krozingen (DE); Thomas Pabst, Mintraching (DE); Rudolf Schmid, Basle (CH)

(73) Assignee: DSM IP Assets B.V. (NL)

( * ) Notice: Subject to any disclaimer, the term of this patent is extended or adjusted under 35 U.S.C. 154(b) by 0 days.

(21) Appl. No.: 10/535,604

(22) PCT Filed: Sep. 29, 2003

(86) PCT No.: PCT/EP03/10789

§ 371 (c)(1),
(2), (4) Date: May 19, 2005

(87) PCT Pub. No.: WO2004/046126

PCT Pub. Date: Jun. 3, 2004

(65) Prior Publication Data

US 2006/0094886 A1  May 4, 2006

(30) Foreign Application Priority Data

Nov. 21, 2002  (EP) ............... 02025989

(51) Int. Cl.
*C07D 311/72* (2006.01)
(52) U.S. Cl. .................................... 549/411
(58) Field of Classification Search ............. 549/411
See application file for complete search history.

(56) References Cited

U.S. PATENT DOCUMENTS 3,708,505 A  1/1973  Greenbaum et al.

FOREIGN PATENT DOCUMENTS

EP  0 949 255 A1  10/1999
WO  WO 03/037883  5/2003

OTHER PUBLICATIONS

Shchegolev et al., Khimiko-Farmatsevticheskii Zhurnal, (1983), vol. 17(1), p. 92-95 (p. 71-73 of the translation).*

* cited by examiner

*Primary Examiner*—Taofiq Solola
(74) *Attorney, Agent, or Firm*—Bryan Cave LLP

(57) ABSTRACT

A process for the manufacture of 3-phytyl-2,5,6-trimethyl-hydroquinone-1-acetate, and optionally therefrom tocopheryl acetate, comprises either C-alkylating 2,3,6-trimethylhydroquinone-1-acetate with isophytol or phytol in the presence of a sulphur(VI) containing catalyst of the formula $R^1SO_2OH$, wherein $R^1$ signifies hydroxy, halogen, lower alkyl, halogenated lower alkyl or aryl, in an aprotic organic solvent, or O-alkylating 2,3,6-trimethylhydroquinone-1-acetate with a phytyl halide in a polar aprotic organic solvent in the presence of a base, and subjecting the so-obtained 4-O-phytyl-2,3,6-trimethylhydroquinone-1-acetate to a rearrangement reaction, and in each case optionally submitting the so-obtained 3-phytyl-2,5,6-trimethylhydroquinone-1-acetate to a ring closure reaction to produce tocopheryl acetate. The invention also includes the novel compound 3-phytyl-2,5,6-trimethylhydroquinone-1-acetate and certain stereoisomers thereof, and also the further novel compound 4-hydroxy-2,3,6-trimethyl-5-[3-(4,8,12-trimethyltridecyl)-but-3enyl]phenyl acetate which itself is one of several isomers of 3-phytyl-2,5,6-trimethylhydroquinone-1-acetate formed by isomerization under the influence of heating, e.g. during its distillation as part of the isolation and purification procedure following its manufacture as indicated above. (All-rac)-α-tocopherol, which may be derived from its acetate, is known to be the most active industrially important member of the vitamin E group.

35 Claims, No Drawings

MANUFACTURE OF TOCOPHERYL ACETATE

This is the National Stage of International Application No. PCT/EP2003/010789, filed Sep. 29, 2003.

The present invention relates to a novel process for the manufacture of tocopheryl acetate and novel intermediates used therein. (All-rac)-α-tocopherol itself is known to be the most active industrially important member of the vitamin E group.

Industrial syntheses of vitamin E (α-tocopherol) are based on the reaction of 2,3,5-trimethylhydroquinone with isophytol, phytol or a phytyl halide: see Ullmann's Encyclopedia of Industrial Chemistry Vol. A27, VCH (1996), pp. 478–488. U.S. Pat. No. 3,708,505 describes the manufacture of d,l-α-tocopherol by carrying out the condensation of 2,3,5-trimethylhydroquinone with isophytol or a derivative thereof in a solvent and using as an acid condensation catalyst a mixture of a Lewis acid, e.g. zinc chloride, and a strong inorganic or organic acid, e.g. p-toluenesulphonic acid; after the condensation reaction the tocopherol can be reacted with acetic anhydride to produce d,l-α-tocopherol acetate. The European patent publication EP 0 949 255 A1 describes the manufacture of d,l-α-tocopherol by the condensation of 2,3,5-trimethylhydroquinone with isophytol in the presence of at most 0.4 weight percent based on the weight of isophytol of a sulphur-containing acid catalyst which is sulphuric acid, methanesulphonic acid, ethanesulphonic acid, trifluoromethanesulphonic acid, p-toluenesulphonic acid or fluorosulphonic acid, so rendering the use of a Lewis acid unnecessary. Furthermore, this condensation is effected in ethylene or propylene carbonate or a mixture of both carbonates, or in a mixture of one or both of the carbonates and a non-polar solvent as the solvent or two-phase solvent system, as appropriate. In this case the conversion of the so-produced tocopherol to its acetate is not described.

Since α-tocopherol is labile under oxidative conditions, it is usually converted into its acetate which is more stable and more convenient to handle. Thus, the manufacture of the usual commercial form of vitamin E, viz. tocopheryl acetate, involves the additional step of esterifying α-tocopherol (as obtained by the acid-catalysed reaction of 2,3,5-trimethylhydroquinone with isophytol, phytol or a phytyl compound, e.g. a halide). In turn, 2,3,5-trimethylhydroquinone is usually obtained from ketoisophorone via 2,3,5-trimethylhydroquinone diacetate and saponification of the latter.

The present invention provides a new approach to the manufacture of tocopheryl acetate. According to this new approach, 2,3,6-trimethylhydroquinone-1-acetate is reacted with either isophytol or phytol to produce 3-phytyl-2,5,6-trimethylhydroquinone-1-acetate, or with a phytyl halide to produce 4-O-phytyl-2,3,6-trimethylhydroquinone-1-acetate which is then submitted to a rearrangement reaction to produce 3-phytyl-2,5,6-trimethylhydroquinone-1-acetate and, finally, the 3-phytyl-2,5,6-trimethylhydroquinone-1-acetate is submitted to a ring closure reaction to obtain tocopheryl acetate. The new approach is shown in the following Reaction Scheme wherein R denotes the remaining portion of the isophytol or phytyl halide molecule 2 or 3, respectively, i.e. 3,7,11-trimethyldodecyl ($R_{15}H_{31}$), and Br is representative of the halogen (Hal) in phytyl halide (3); Furthermore, isophytol (2) is representative of isophytol and phytol in this Reaction Scheme.

Reaction Scheme

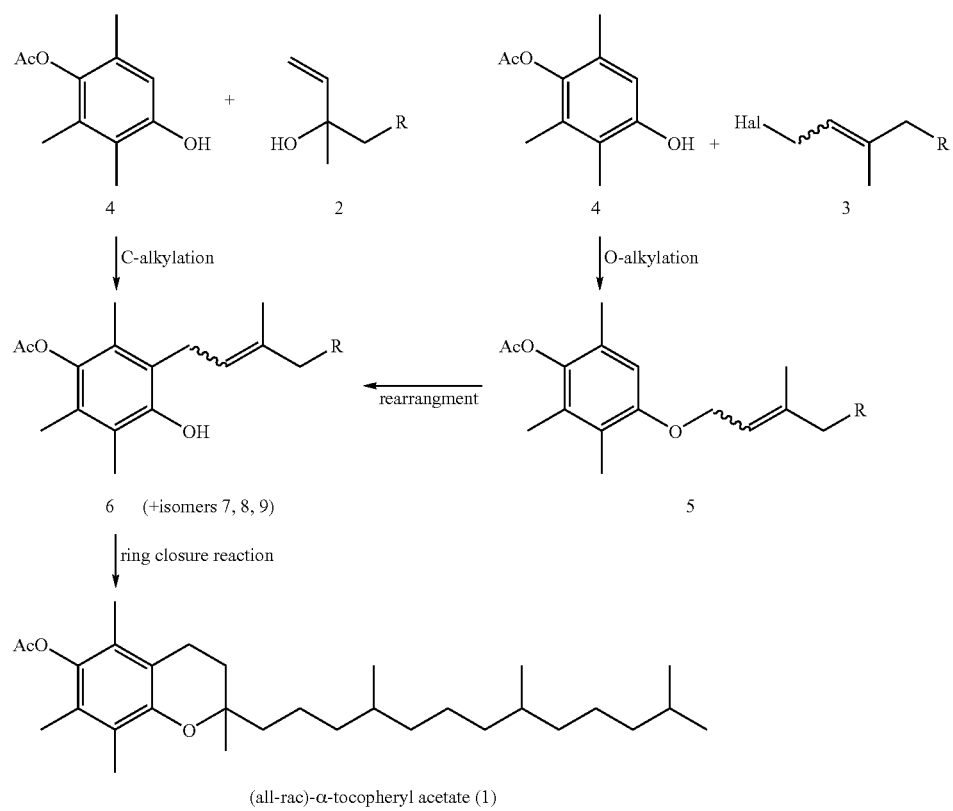

(all-rac)-α-tocopheryl acetate (1)

Whereas the Reaction Scheme illustrates the manufacture of (all-rac)-α-tocopheryl acetate the invention is not limited to that particular stereochemical configuration; other stereochemical configurations can be obtained by using the starting material phytol, isophytol or phytyl halide which has the appropriate stereochemical configuration. Thus, (RS,R,R)-α-tocopheryl acetate will be obtained when using (R,R)-phytol, (R,R,R)-isophytol, or (S,R,R)-isophytol or (RS,R,R)-isophytol or a (R,R)-phytyl halide.

The present invention relates to a process for the manufacture of 3-phytyl-2,5,6-trimethylhydroquinone-1-acetate (6), and optionally therefrom tocopheryl acetate (1), which comprises either (a) C-alkylating 2,3,6-trimethylhydroquinone-1-acetate (4) with isophytol (2) or phytol in the presence of a sulphur (VI) containing catalyst of the formula $R^1SO_2OH$, wherein $R^1$ signifies hydroxy, halogen, aliphatic hydrocarbyl (lower alkyl), aliphatic halocarbyl (halogenated lower alkyl) or aromatic hydrocarbyl (aryl), in an aprotic organic solvent, or (b) O-alkylating 2,3,6-trimethylhydroquinone-1-acetate (4) with a phytyl halide (3) in a polar aprotic organic solvent in the presence of a base, and subjecting the so-obtained 4-O-phytyl-2,3,6-trimethylhydroquinone-1-acetate (5) to a rearrangement reaction, and in each case optionally submitting the so-obtained 3-phytyl-2,5,6-trimethylhydroquinone-1-acetate (6) to a ring closure reaction to produce tocopheryl acetate.

In another aspect, the present invention relates to a process for the manufacture of tocopheryl acetate (1) which comprises submitting 3-phytyl-2,5,6-trimethylhydroquinone-1-acetate (6), independently of its means of manufacture, to a ring closure reaction to produce tocopheryl acetate (featuring the chroman ring system).

In still another aspect, the present invention relates to the novel compound 3-phytyl-2,5,6-trimethylhydroquinone-1-acetate (6), including its stereoisomers (E,all-rac)-3-phytyl-2,5,6-trimethylhydroquinone-1-acetate, (Z,all-rac)-3-phytyl-2,5,6-trimethylhydroquinone-1-acetate, (E,R,R)-3-phytyl-2,5,6-trimethylhydroquinone-1-acetate and (Z,R,R)-3-phytyl-2,5,6-trimethylhydroquinone-1-acetate.

In the C-alkylation of the compound (4) in accordance with the present invention [variant (a)] the isophytol or phytol starting material may have the stereochemical configuration derived from natural phytol (R,R), or may have any other stereochemical configuration; e.g. the all-rac configuration.

The C-alkylation is carried out using a sulphur(VI) containing catalyst of the formula $R^1SO_2OH$, wherein $R^1$ is hydroxy, halogen, lower alkyl, halogenated lower alkyl or aryl. The term "lower alkyl" as such or in "halogenated lower alkyl" indicates in particular a (halogenated) alkyl group containing 1 to 4 carbon atoms, preferably 1 or 2 in the case of "lower alkyl", or preferably a single carbon atom in the case of "halogenated lower alkyl". If containing 3 or more carbon atoms the (halogenated) lower alkyl group can be straight chain or branched, examples of branched alkyl groups being isopropyl and tert. butyl. In "halogenated lower alkyl" one or more of the same or mixed halogen atoms may be present as the halogen substituent(s). Any halogen substituent is especially fluorine or chlorine, the preferred halogen substituent being fluorine, and in this context the most preferred halogenated lower alkyl group is trifluoromethyl. In the case where R is aryl this is preferably phenyl or substituted phenyl, any substituents of phenyl being in particular one or more lower alkyl, preferably methyl, groups. Most preferably, however, aryl is phenyl or p-tolyl. Accordingly, the sulphur(VI) containing catalyst of the formula $R^1SO_2OH$ is in particular sulphuric acid, fluorosulphonic acid, methane- or ethanesulphonic acid, trifluoromethanesulphonic acid or benzene- or p-toluenesulphonic acid, respectively. Of these, a sulphur(VI) containing catalyst of the formula $R^1SO_2OH$ which is particularly effective in two-phase solvent systems, e.g. trifluoromethanesulphonic acid or p-toluenesulphonic acid, is most preferred.

The aprotic organic solvents in which the C-alkylation reaction is carried out are either polar aprotic organic solvents or non-polar aprotic organic solvents. Suitable classes of polar aprotic organic solvents include aliphatic and cyclic ketones, e.g. diethyl ketone and isobutyl methyl ketone, and respectively cyclopentanone and isophorone; aliphatic and cyclic esters, e.g. ethyl acetate and isopropyl acetate, and respectively γ-butyrolactone; and dialkyl and alkylene (cyclic) carbonates, e.g. dimethyl carbonate and diethyl carbonate, and, respectively, ethylene carbonate and propylene carbonate. Suitable classes of non-polar aprotic organic solvents in which the C-alkylation is alternatively carried out are aliphatic hydrocarbons, e.g. hexane, heptane and octane, and aromatic hydrocarbons, e.g. benzene, toluene and the xylenes. The reaction can be effected in a single solvent phase, especially in a polar aprotic organic solvent, e.g. in toluene, alone as the solvent, or in a biphasic solvent system, especially one containing both kinds of aprotic organic solvents, e.g. in ethylene and/or propylene carbonate as the polar aprotic, and hexane, heptane or octane as the non-polar aprotic organic solvent.

The catalyst may be present in an amount of from about 0.01 mol. % to about 1 mol. %, preferably in an amount of about 0.05 mol. % to about 0.1 mol. %, based on the molar amount of phytol or isophytol, whichever is employed.

Furthermore, the molar ratio of 2,3,6-trimethylhydroquinone-1-acetate (this generally being the reactant used in excess) to isophytol/phytol present in the reaction mixture of the C-alkylation conveniently extends from about 2.2:1 to about 1:1, preferably from about 2:1 to about 1:1, and is most preferably about 1.5:1 to about 1:1.

Suitably, the C-alkylation is effected at temperatures from about 20° C. to about 160° C., preferably from about 80° C. to about 150° C., and most preferably from about 100° C. to about 127° C.

Conveniently, about 0.25 to 6 ml, preferably about 0.5 to 3 ml, of organic solvent are used per 1 mmol of isophytol or phytol, whichever is employed, these amounts referring to total solvent, i.e. regardless of whether the C-alkylation reaction is effected in a single phase or in a biphasic solvent system.

If the process is carried out in a biphasic solvent system, especially one consisting of a polar aprotic organic solvent, e.g. a cyclic carbonate such as ethylene or propylene carbonate, and a non-polar aprotic organic solvent, e.g. an aliphatic hydrocarbon such as heptane, then the volume ratio of the non-polar solvent to the polar solvent is conveniently in the range from about 1:5 to about 30:1, preferably from about 1:3 to about 20:1, most preferably about 10:1 to about 15:1 The preferred solvent is the biphasic solvent system of ethylene carbonate and heptane.

Moreover, and in order to reduce as much as possible the contact of the reaction mixture with the ambient moisture, which generally exerts a negative effect on the course of the reaction, the process can be carried out under an inert gas atmosphere, preferably gaseous nitrogen or argon.

The C-alkylation reaction can be carried out batchwise or continuously, preferably continuously, and in general operationally in a very simple manner, for example by adding isophytol or phytol, as such or in solution, portionwise to a suspension or solution of the 2,3,6-trimethylhydroquinone-1-acetate and the catalyst. The isophytol or phytol is conveniently added continuously at a rate of about 0.2 to about 1 ml/minute, preferably about 0.4 to about 0.8 ml/minute. After completion of the isophytol/phytol addition the reaction mixture is suitably heated at the reaction temperature for a further about 10 to about 60 minutes, preferably about 20 to about 30 minutes. The working-up can be effected by procedures conventionally used in organic chemistry.

The process variant (b) of the present invention for manufacturing 3-phytyl-2,5,6-trimethylhydroquinone-1-acetate (6) in two reaction steps, namely the O-alkylation followed by the rearrangement of the so-obtained 4-O-phytyl-2,3,6-trimethylhydroquinone-1-acetate (5), involves for the O-alkylation of the starting 2,3,6-trimethylhydroquinone-1-acetate (4) a phytyl halide (3), which is suitably the bromide or the chloride, but preferably phytyl bromide. As in the case of isophytol or phytol in the above-described C-alkylation, the phytyl halide reactant in the present O-alkylation may have the stereochemical configuration of natural phytol (R,R) or may be of any other stereochemical configuration, e.g. the all-rac form.

The O-alkylation can be performed in principle using conventional conditions for the alkylation of phenolic systems, e.g. as described in Chem. Lett. 1982, 1131–1134. In the present case it is suitably effected in the presence of a base such as sodium hydride and in the same sort of polar aprotic organic solvent as used for the above-described C-alkylation, or in a dialkylformamide. Preferred solvents are dimethylformamide and dibutylformamide.

The base is generally used in excess relative to the amount of 2,3,6-trimethylhydroquinone-1-acetate, in particular in a molar excess of about 5 to about 30%, preferably about 10 to about 20%.

Suitably, the O-alkylation is effected at temperatures from about −20° C. to about +30° C., preferably from about −10° C. to about +15° C., and most preferably from about 100° C. to about 127° C.

The O-alkylation reaction can be carried out batchwise or continuously, preferably continuously, and in general operationally in a very simple manner, for example by adding the phytyl halide, as such or in solution, portionwise to a suspension or solution of the 2,3,6-trimethylhydroquinone-1-acetate and the base, suitably over a period of from about 20 to about 80 minutes, preferably from about 30 to about 60 minutes, and allowing a further reaction time thereafter.

Moreover, and in order to reduce as much as possible the contact of the reaction mixture with the atmospheric oxygen, which generally exerts a negative effect on the course of the reaction, the process is suitably carried out under an inert gas atmosphere, preferably gaseous nitrogen or argon.

The working-up of the mixture after completion of the reaction, if the isolation of the so-obtained 4-O-phytyl-2,3,6-trimethylhydro-quinone-1-acetate (5) before its rearrangement to 3-phytyl-2,5,6-trimethylhydroquinone-1-acetate (6) in the second step of this variant (b) is desired, can be effected by procedures conventionally used in organic chemistry.

The subsequent rearrangement reaction of the 4-O-phytyl-2,3,6-trimethylhydroquinone-1-acetate (5) as the second step of the process variant (b) is suitably performed in the presence of an acidic catalyst, in particular a Friedel-Crafts catalyst such as boron trifluoride etherate, in an aprotic organic solvent and at temperatures below room temperature (below about 20° C.).

Examples of the aprotic organic solvent are alkanes, e.g. hexane, halogenated alkanes, e.g. carbon tetrachloride, and mixtures of these two types of aprotic organic solvents. The preferred solvent is a mixture of hexane and carbon tetrachloride.

The rearrangement reaction is preferably performed at temperatures from about −28° C. to about −23° C.

The pressure under which the rearrangement reaction is carried out is not critical, the reaction conveniently being carried out at atmospheric pressure. Furthermore, the process is conveniently carried out under an inert gas atmosphere, preferably gaseous nitrogen or argon.

The rearrangement reaction can be carried out batchwise or continuously, and in general operationally in a very simple manner, e.g. by adding the catalyst, as such or suspended in the aprotic organic solvent, portionwise or continuously to a mixture of the 4-O-phytyl-2,3,6-trimethylhydroquinone-1-acetate (5) and the (further) aprotic organic solvent. After completion of the addition and an appropriate subsequent reaction period the isolation of the product and its purification, which is generally not required, can be effected by procedures conventionally used in organic chemistry.

The ring closure of 3-phytyl-2,5,6-trimethylhydroquinone-1-acetate (6) in accordance with the invention, either following the C-alkylation according to process variant (a) or the O-alkylation and the subsequent rearrangement reaction according to process variant (a), or independently of the means of manufacture of the 3-phytyl-2,5,6-trimethylhydroquinone-1-acetate, can be effected by treating said acetate with an acidic catalyst in the presence or absence of a solvent.

Preferred solvents, if used, are those polar aprotic organic solvents which are specified above in connection with the C-alkylation of process variant (a), viz. aliphatic and cyclic ketones, e.g. diethyl ketone and isobutyl methyl ketone, and respectively cyclopentanone and isophorone; aliphatic and cyclic esters, e.g. ethyl acetate and isopropyl acetate, and respectively γ-butyrolactone; and dialkyl or alkylene (cyclic) carbonates, e.g. dimethyl carbonate and diethyl carbonate, and, respectively, ethylene carbonate and propylene carbonate.

The preferred acidic catalysts are also those catalysts (of the formula $R^1SO_2OH$) specified above for the C-alkylation. In a preferred embodiment of the ring closure, whereby the C-alkylation [process variant (a)] is employed to manufacture the 2,3,6-trimethylhydroquinone-1-acetate (4), the same catalyst and the same solvent are used in both the C-alkylation of 2,3,6-trimethylhydroquinone-1-acetate (4) and in the subsequent ring closure of the so-obtained 3-phytyl-2,5,6-trimethylhydroquinone-1-acetate (6).

For the ring closure reaction the catalyst is suitably present in an amount of from about 0.01 mol. % to about 10 mol. %, preferably in an amount of about 0.1 to about 5 mol. %, based on the molar amount of the 3-phytyl-2,5,6-trimethylhydroquinone-1-acetate (6).

Furthermore, the ring closure reaction is conveniently effected at temperatures from about 20° C. to about 160° C., preferably from about 80° C. to about 140° C.

It has been found that the 3-phytyl-2,5,6-trimethylhydroquinone-1-acetate (6) may isomerize under the influence of heating, e.g. during its distillation as part of the isolation and purification procedure following its manufacture in the C-alkylation reaction (process variant (a)] or the O-alkylation reaction and subsequent rearrangement reaction [process variant (b)], to form the isomers:

(Z)-acetic acid 4-hydroxy-2,3,6-trimethyl-5-(3,7,11,15-tetramethylhexadec-3-enyl)-phenyl ester [7; alternately named (Z)-4-hydroxy-2,3,6-trimethyl-5-(3,7,11,15-tetramethylhexadec-3-enyl)-phenyl acetate],
(E)-acetic acid 4-hydroxy-2,3,6-trimethyl-5-(3,7,11,15-tetramethylhexadec-3-enyl)-phenyl ester [8; alternately named (E)-4-hydroxy-2,3,6-trimethyl-5-(3,7,11,15-tetramethylhexadec-3-enyl)-phenyl acetate], and
acetic acid 4-hydroxy-2,3,6-trimethyl-5-[3-(4,8,12-trimethyltridecyl)-but-3-enyl]phenyl ester (9; alternately named 4-hydroxy-2,3,6-trimethyl-5-[3-(4,8,12-trimethyltridecyl)-but-3-enyl]phenyl acetate]

Their formulae, in which R has the significance given above, are:

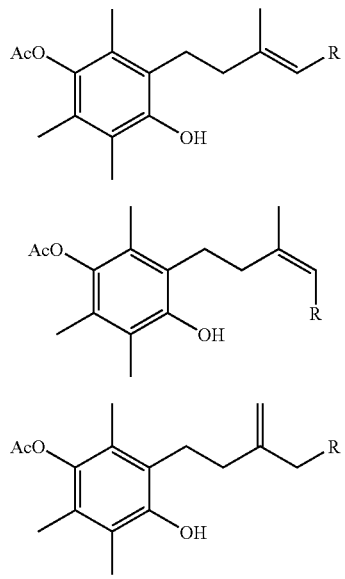

These isomers can be cyclized or ring closed to form α-tocopheryl acetate in the same manner, i.e. under the same conditions, as described above for the ring closure of 3-phytyl-2,5,6-trimethylhydroquinone-1-acetate (6). Accordingly, the invention also includes the cyclization of an isomer (7), (8) or (9), or a mixture comprising two or three of said isomers, either as such or together with (6), to α-tocopheryl acetate. Furthermore, of these three compounds the compound 9 is a novel compound, and, as such is also an object of the present invention.

The starting compound 2,3,6-trimethylhydroquinone-1-acetate (4) in the process of the present invention may be obtained, e.g. by selective hydrolysis of 2,3,5-trimethylhydroquinone-diacetate as described in EP 1 239 045.

The following Examples illustrate the present invention.

EXAMPLE 1

In a four-necked flask equipped with stirrer, water separator and reflux condenser 19.7 g (100 mmol) of trimethylhydroquinone-1-acetate and 25 ml of solvent (toluene, n-butyl acetate or diethyl ketone) were heated with stirring under an argon atmosphere to reflux temperature (oil bath temperature 140–145° C.). After the addition of the catalyst (p-toluenesulphonic acid or trifluoromethanesulphonic acid) in an amount 0.1 mol. % based on the amount of acetate (same mmol as the amount of subsequently added isophytol) 36.4 ml (100 mmol) of isophytol were added at a rate of 0.8 ml/minute. The reaction mixture was heated under reflux for 30 minutes after completion of the addition of the isophytol and then cooled and finally evaporated under reduced pressure. A viscous oil was obtained which was analysed for its (all-rac)-α-tocopheryl acetate content and so the yield thereof determined. For the yields of (all-rac)-α-tocopheryl acetate under the various reaction conditions (employed catalyst and solvent) see Table 1.

EXAMPLE 2

In a four-necked flask equipped with stirrer, water separator and reflux condenser, 19.7 g (100 mmol) of trimethylhydroquinone-1-acetate and 25 ml of γ-butyrolactone were heated with stirring under an argon atmosphere to about 110° C. (oil bath temperature 115° C.). After the addition of catalyst (p-toluenesulphonic acid, sulphuric acid, methanesulphonic acid, trifluoromethanesulphonic acid or fluorosulphonic acid) 36.4 ml (100 mmol) of isophytol were added at a rate of 0.8 ml/minute. The reaction mixture was heated under reflux for 30 minutes after completion of the addition of the isophytol. The reaction mixture was cooled to 80° C. and extracted three times with 50 ml of heptane. The combined heptane phases were evaporated under reduced pressure to afford a viscous oil. This was analysed in each case for its (all-rac)-α-tocopheryl acetate content and so the yield thereof determined. For the yields of (all-rac)-α-tocopheryl acetate under the various reaction conditions (employed catalyst and solvent) see Table 1.

EXAMPLE 3

In a four-necked flask equipped with stirrer, water separator and a reflux condenser, 29.5 g (150 mmol) of trimethylhydroquinone-1-acetate, 120 g of ethylene carbonate and 150 ml of heptane were heated with stirring under an argon atmosphere to reflux (oil bath temperature 140° C.). After the addition of catalyst (p-toluenesulphonic acid, sulphuric acid, methanesulphonic acid, trifluoromethanesulphonic acid or fluorosulphonic acid) 36.4 ml (100 mmol) of isophytol were added at a rate of 0.8 ml/minute. Approximately 1.8 ml of water were collected after complete addition of the isophytol. The heptane was distilled off within about 20 minutes. Afterwards the reaction mixture was heated for 30 minutes at 125–130° C. The reaction mixture was cooled down to 80° C., 150 ml of heptane were added to the carbonate phase and the reaction mixture was stirred for an additional 10 minutes at 80–90° C. Stirring was discontinued and the reaction mixture was cooled to 5° C. The heptane layer was separated and evaporated under reduced pressure, affording a viscous oil. This was analysed in each case for its (all-rac)-α-tocopheryl acetate content and so the yield thereof determined. For the yields of (all-rac)-α-tocopheryl acetate under the various reaction conditions (employed catalyst) see Table 1.

TABLE 1

Reaction of isophytol (IP) and trimethylhydroquinone-1-acetate (TMHQ-1-A) to (all-rac)-α-tocopheryl acetate (1) according to the Examples 1–3

| Example | Catalyst | Mol. % | Solvent | % yield of 1 | % yield of vit. E |
|---|---|---|---|---|---|
| 1 | p-TsOH | 0.1 | toluene | 20.4 | 0.0 |
| 1 | CF$_3$SO$_3$H | 0.1 | toluene | 62.6 | 7.8 |

TABLE 1-continued

Reaction of isophytol (IP) and trimethylhydroquinone-1-acetate (TMHQ-1-A) to (all-rac)-α-tocopheryl acetate (1) according to the Examples 1–3

| Example | Catalyst | Mol. % | Solvent | % yield of 1 | % yield of vit. E |
|---------|----------|--------|---------|--------------|-------------------|
| 1 | $CF_3SO_3H$ | 0.1 | DEK | 60.7 | 3.6 |
| 1 | $CF_3SO_3H$ | 0.1 | BuAc | 54.8 | 6.7 |
| 2 | p-TsOH | 0.1 | Bulac | 14.2 | 0.3 |
| 2 | $H_2SO_4$ | 0.1 | Bulac | 29.5 | 1.8 |
| 2 | $CH_3SO_3H$ | 0.1 | Bulac | 10.2 | 0.1 |
| 2 | $CF_3SO_3H$ | 0.1 | Bulac | 50.0 | 15.7 |
| 2 | $FSO_3H$ | 0.1 | Bulac | 15.9 | 0.7 |
| 3 | p-TsOH | 0.1 | EC/hept | 78.1 | 0.6 |
| 3 | p-TsOH | 2.5 | EC/hept | 80.6 | 2.2 |
| 3 | $H_2SO_4$ | 0.1 | EC/hept | 67.5 | 2.2 |
| 3 | $CH_3SO_3H$ | 0.1 | EC/hept | 20.0 | 0.0 |
| 3 | $CH_3SO_3H$ | 2.5 | EC/hept | 79.4 | 4.0 |
| 3 | $CF_3SO_3H$ | 0.1 | EC/hept | 81.9 | 3.5 |
| 3 | $FSO_3H$ | 0.1 | EC/hept | 67.0 | 3.0 |

The amount of catalyst is based on that of isophytol; the molar TMHQ-1-A/IP ratio was 1:1 with the exception of PC and EC, where a 1.5:1 ratio was used; p-toluenesulphonic acid (p-TsOH) was used as its monohydrate; abbreviations used include vit. E=vitamin E (unesterified), EC=ethylene carbonate, hept=heptane, DEK=diethyl ketone, BuAc=n-butyl acetate, Bulac=γ-butyrolactone; the yields are in each case based on isophytol.

EXAMPLE 4

In a four-necked flask equipped with stirrer, water separator and reflux condenser 29.5 g (150 mmol) of 2,3,6-trimethylhydroquinone-1-acetate, 120 g of ethylene carbonate, and 150 ml of heptane were heated under an argon atmosphere to reflux (oil bath temperature 140° C.). After the addition of catalyst (p-toluenesulphonic acid, trifluoromethanesulphonic acid, methanesulphonic acid, fluorosulphonic acid or sulphuric acid) 36.4 ml (100 mmol) of isophytol were added at a rate of 0.8 ml/minute. Approximately 1.8 ml of water were separated after the complete addition of the isophytol. Afterwards the reaction mixture was heated for 15 minutes under reflux. Stirring was then discontinued and the reaction mixture cooled to 5° C. The heptane layer was separated and evaporated under reduced pressure, affording a viscous oil. This was analysed in each case for its (E,Z)-(all-rac)-3-phytyl-2,5,6-trimethylhydroquinone-1-acetate (6) content and the E:Z ratio, and so the yield of 6 and the E:Z ratio determined. For the yields of (E,Z)-(all-rac)-3-phytyl-2,5,6-trimethylhydroquinone-1-acetate (E:Z=2.2-2.4:1), based in each case on isophytol, using the various catalysts in various amounts see Table 2.

TABLE 2

C-alkylation reaction of TMHQ-1-A

| Catalyst | Mol. % | % yield of 6 | % yield of 1 |
|----------|--------|--------------|--------------|
| p-TsOH | 0.1 | 72.5 | 11.7 |
| $CF_3SO_3H$ | 0.01 | 46.4 | 34.4 |
| $CH_3SO_3H$ | 0.1 | 73.4 | 4.1 |
| $FSO_3H$ | 0.05 | 62.3 | 17.4 |
| $H_2SO_4$ | 0.1 | 51.8 | 29.3 |
| $H_2SO_4$ | 0.05 | 74.5 | 1.4 |
| $CH_3SO_3H$ | 2.5 | 79.4 | 34.4 |

The amount of catalyst is based on that of isophytol, p-TsOH was used as its monohydrate; the abbreviations used in Table 2 include those used in Table 1, under which their meanings are given; (1)=(all-rac)-α-tocopheryl acetate.

EXAMPLE 5

29.43 g (150 mmol) of 2,3,6-trimethylhydroquinone-1-acetate (4), 120 g of ethylene carbonate, 21.14 mg (0.1 mol %) of p-toluenesulphonic acid monohydrate and 150 ml of heptane were heated to 100° C. (oil bath temperature 130° C.) in a four-necked flask equipped with stirrer, water separator and reflux condenser. Isophytol (36.18 ml, 100 mmol) was added at a rate of 0.8 ml/minute under reflux. After heating for an additional 5 minutes the reaction mixture was cooled to room temperature. The heptane layer was separated and the solvent evaporated under reduced pressure (40° C., 10 mbar). 49.43 g of a yellowish oil were obtained which contained, according to gas chromatography (GC), 68% of (E,Z)-(all-rac)-3-phytyl-2,5,6-trimethylhydroquinone-1-acetate (6), E:Z-ratio 2.2:1, yield of 6 based on 471%, and 2% of (all-rac)-α-tocopheryl-acetate.

The oil obtained as described above was purified further by column chromatography on silica gel [Merck 109385.1000, Kieselgel 60 (0.040-0.063 mm); eluent 1 l of 100% n-hexane→1 l of n-hexane/diethyl ether 10:1→1.7 l of n-hexane/$Et_2O$ (10:2)], to afford (6) as a light yellow oil of 89.4% purity, E:Z-ratio about 3:1. The oil still contained 0.70% of (all-rac)-α-tocopheryl acetate.

The E- and Z-isomers could be separated by high performance liquid chromatography (HPLC) using a Spherisorb® Si 5 μm column and isopropyl acetate/n-hexane (4:100) as the mobile phase.

E-Isomer:

$^1$H-NMR (CDCl$_3$, 400 MHz): δ=0.78–0.93 (m, 12H, 4 CH$_3$), 0.97–1.57 (m, 19 aliph. H.), 1.80 (s, 3H, =CC$\underline{H}_3$CH$_2$), 1.98 (t, J=7.4 Hz, 2H, =CCH$_3$C$\underline{H}_2$), 2.04, 2.07, 2.14 (each s, 3H, Ar—CH$_3$), 2.33 (s, 3H, CH$_3$CO), 3.36 (d, J=6.8 Hz, 2H, ArC$\underline{H}_2$), 5.08 (s, 1H, OH), 5.13 (t, J=6.6 Hz, 1H, C$\underline{H}$=);

IR (film): 3500s, 2927s, 2868s, 1762s, 1745s, 1577w, 1462s, 1369s, 1225s, 1075m, 1010W, 514s;

Z-Isomer:

$^1$H-NMR (CDCl$_3$, 400 MHz): δ=0.79–0.96 (m, 12H, 4 CH$_3$), 1.00–1.57 (m, 19 aliph. H), 1.72 (s, 3H, =CC$\underline{H}_3$CH$_2$), 2.03, 2.06, 2.14 (each s, 3H, Ar—CH$_3$), 2.20 (t, J=7.8 Hz, 2H, =CCH$_3$C$\underline{H}_2$), 2.33 (s, 3H, CH$_3$CO), 3.36 (d, J=6.4 Hz, 2H, ArC$\underline{H}_2$), 5.06 (s, 1H, OH), 5.13 (t, J=6.6 Hz, 1H, C$\underline{H}$=);

IR (film): 3496s, 2926s, 2868s, 1761s, 1745s, 1577w, 1462s, 1369s, 1227s, 1076m, 1056m, 1010w, 516s;

EXAMPLE 6

From the (E,Z)-(all-rac)-3-phytyl-2,5,6-trimethylhydroquinone-1-acetate as obtained in Example 5, inter alia the isomer (all-rac)-acetic acid 4-hydroxy-2,3,6-trimethyl-5-[3-(4,8,12-trimethyltridecyl)-but-3-enyl]phenyl ester (9) was identified and chromatographically isolated as follows:

In a first step traces of ethylene carbonate, phytadienes, and 2,3,6-trimethylhydroquinone-1-acetate were distilled off at 90° C. and 2.5×10$^{-2}$ mbar. The distilled material was submitted to HPLC using a Spherisorb® Si 5 μm column and isopropyl acetate/n-hexane (4:100) as the mobile phase. Besides the isomers (Z,RS,RS)-acetic acid 4-hydroxy-2,5,6-trimethyl-3-(3,7,11,15-tetramethylhexadec-3-enyl)-phenyl ester (7) and (E,RS,RS)-acetic acid 4-hydroxy-2,5,6-trimethyl-3-(3,7,11,15-tetramethylhexadec-3-enyl)-phenyl ester (8), the isomer (all-rac)-acetic acid 4-hydroxy-2,5,6-trimethyl-3-[3-(4,8,12-trimethyltridecyl)-but-3-enyl]phenyl ester (9) was identified [HP gas chromatograph (6890) with split injector and HP autosampler (7673), HP mass selective detector (5973); column: 5% phenyl-methyl siloxane fused silica (Restek), 30 m×0.28 mm, film 0.5 µm; carrier gas:He; flow 1.5 ml/minute (constant flow); split ratio approx. 1:25]:

The analytical data for the separated (all-rac)-acetic acid 4-hydroxy-2,3,6-trimethyl-5-[3-(4,8,12-trimethyltridecyl)-but-3-enyl]phenyl ester (9) are as follows:

$^1$H-NMR (CDCl$_3$, 400 MHz): δ=0.77–0.92 (m, 12H, 4 CH$_3$), 0.98–1.55 (m, 17 aliph. H), 2.14, 2.18, 2.72 (each s, 3H, Ar—CH$_3$), 2.02–2.09 (m, 2H, =CCH$_2$), 2.14–2.18 (m, 2H, =CCH$_2$) 2.33 (s, 3H, CH$_3$CO), 2.72–2.77 (m, 2H, ArC H$_2$), 4.58 (s, 1H, OH), 4.80, 4.83 (each s, 1H, CH$_2$=);

GC-MS (EI): m/z=430 [M$^+$-C$_2$H$_2$O, 75%], 207 [M$^+$-C$_{15}$H$_{32}$, 29%], 165[430-C$_{15}$H$_{32}$, 100%].

EXAMPLE 7

A 0.34 to 0.52 M stock solution of (E/Z)-(all-rac)-3-phytyl-2,5,6-trimethylhydroquinone-1-acetate (6) in the used solvent (heptane, toluene, diethyl ketone, n-butyl acetate or γ-butyrolactone) was prepared.

2.5 ml of this solution (or in the case of heptane 1.5 ml thereof and additionally 1.2 g of ethylene carbonate) were transferred to a Schlenk tube under argon, the catalyst (methanesulphonic acid or trifluoromethanesulphonic acid) was added, and the reaction mixture was heated for 1 hour at 100° C. (oil bath temperature). Then the solution was cooled to room temperature and in the case of toluene, diethyl ketone and n-butyl acetate the solvent distilled off under reduced pressure. In the case of γ-butyrolactone the reaction mixture was extracted three times with about 1.5 ml of heptane. In the case of the biphasic solvent system ethylene carbonate and heptane the layers were separated and the heptane phase was concentrated in vacuo. In each case the remaining oil or solution was analysed for its (all-rac)-α-tocopheryl acetate (1) content and so the yield thereof determined. For the yields of (all-rac)-α-tocopheryl acetate under the various reaction conditions (employed catalyst, catalyst amount based on the starting material 6, and solvent) see Table 3.

TABLE 3

Ring closure reaction of (E,Z)-(all-rac)-3-phytyl-2,5,6-trimethylhydroquinone-1-acetate (6)

| Catalyst | Mol. % | Solvent | % un-reacted 6 | % yield of 1 | % yield of vit. E |
|---|---|---|---|---|---|
| CH$_3$SO$_3$H | 0.1 | EC/hept | 87.9 | 0.9 | 0 |
| CH$_3$SO$_3$H | 1.16 | toluene | 44.5 | 53.8 | 0 |
| CH$_3$SO$_3$H | 0.116 | DEK | 97.5 | 0.5 | 0 |
| CH$_3$SO$_3$H | 0.1 | BuAc | 99.6 | 0.6 | 0 |
| CH$_3$SO$_3$H | 0.1 | Bulac | 94.0 | 2.2 | 0 |
| CF$_3$SO$_3$H | 0.1 | EC/hept | 18.6 | 84.9 | 0 |
| CF$_3$SO$_3$H | 1.16 | toluene | 0 | 96.1 | 3.3 |
| CF$_3$SO$_3$H | 0.116 | DEK | 2.7 | 97.3 | 0.2 |
| CF$_3$SO$_3$H | 0.1 | BuAc | 17.0 | 84.7 | 0.1 |
| CF$_3$SO$_3$H | 0.1 | Bulac | 0 | 100.9 | 1.7 |

The abbreviations used in Table 3 include those used in Table 1, under which their meanings are given.

EXAMPLE 8

In analogy to the procedure of Example 7 but increasing the reaction time and the amount of catalyst (methanesulphonic acid, p-toluenesulphonic acid monohydrate or sulphuric acid) the results presented in Table 4 were obtained:

TABLE 4

Ring closure reaction of (E,Z)-(all-rac)-3-phytyl-2,5,6-trimethylhydroquinone-1-acetate (6)

| Catalyst | Reaction time [minutes] | Temp.(bath) ° C. | Mol. % | Solvent | % yield of 1 | % yield of vit. E |
|---|---|---|---|---|---|---|
| CH$_3$SO$_3$H | 180 | 120 | 5.0 | toluene | 100 | 0.8 |
| CH$_3$SO$_3$H | 180 | 120 | 5.0 | DEK | 72.9 | 0.1 |
| CH$_3$SO$_3$H | 180 | 120 | 5.0 | BuAc | 69.4 | 0.2 |
| CH$_3$SO$_3$H | 180 | 120 | 5.0 | Bulac | 97.9 | 0.8 |
| p-TsOH | 120 | 100 | 2.56 | EC/hept | 96.3 | 0.1 |
| H$_2$SO$_4$ | 180 | 100 | 6.25 | EC/hept | 97.8 | 1.5 |
| H$_2$SO$_4$ | 120 | 120 | 2.5 | EC/hept | 100.3 | 0.6 |

The amount of catalyst is based on that of the starting material 6, the abbreviations used in Table 2 include those used in Table 1, under which their meanings are given; (1)=(all-rac)-α-tocopheryl acetate.

EXAMPLE 9

1.4 mg (3.15×10$^{-3}$ mmol) of (all-rac)-acetic acid 4-hydroxy-2,3,6-trimethyl-5-[3-(4,8,12-trimethyltridecyl)-but-3-enyl]phenyl ester (9) were dissolved in 0.1 ml of propylene carbonate and 0.2 ml of heptane. After addition of 0.5 mg (2.63×10$^{-3}$ mmol) of p-toluenesulphonic acid monohydrate the reaction mixture was heated for 90 minutes to 120° C. (oil bath temperature). A gas chromatogram of the heptane phase identified the cyclisation product (all-rac)-α-tocopheryl acetate in 98.5% purity (GC-area %).

EXAMPLE 10

To 2.1 g (43.7 mmol) of sodium hydride dispersion (50% in mineral oil) which had been freed from mineral oil by washing with hexane there were added under an argon atmosphere 90 ml of dimethylformamide and, after cooling to about 5° C., 7.38 g (38 mmol) of 2,3,6-trimethylhydroquinone-1-acetate. After about 30 minutes, 16.4 g (45.6 mmol) of phytyl bromide (freshly prepared from natural phytol) in 30 ml of dimethylformamide were added dropwise at 0° C. over a period of 15 minutes. The reaction mixture was stirred for 1 hour while warming to ambient temperature, and then quenched with 300 ml of deionized water and 200 m ml of diethyl ether. The organic layer was separated and the aqueous layer extracted with diethyl ether. The combined organic layers were washed successively with cold 2N aqueous sodium hydroxide, water and brine, dried over anhydrous sodium sulphate, filtered and evaporated to afford 20.0 g of an amber liquid. Flash chromatography of this material on silica gel using hexanes/ethyl acetate 1%→3% yielded 15.6 g of (E,R,R)-4-O-phytyl-2,3,6-trimethylhydroquinone-1-acetate, as a pale yellow oil; [α]$_D^{25}$=−0.44° (1.13% in hexane).

EXAMPLE 11

In analogy to Example 10, a different batch of natural phytol containing small amounts of (Z,R,R)-phytol was used. After conversion of the phytol to phytyl bromide, and subsequent O-alkylation reaction with 2,3,6-trimethylhydroquinone-1-acetate, (E/Z,R,R)-4-O-phytyl-2,3,6-trimethylhydroquinone-1-acetate (5) was obtained after chromatographic purification as a yellow oil having an E:Z ratio of 98.7:1.3 (HPLC analysis).

EXAMPLE 12

In further analogy to Example 10, a batch of (B,Z,all-rac)-phytol was used for the conversion to phytyl bromide and the subsequent O-alkylation reaction with 2,3,6-trimethylhydroquinone-1-acetate afforded (E/Z,all-E)-4-O-phytyl-2,3,6-trimethylhydroquinone-1-acetate (5). After chromatographic purification of the obtained yellow oil the product was shown by HPLC analysis to have an E:Z ratio of 78.3:21.7.

EXAMPLE 13

6.76 g (14.3 mmol) of (E,R,R)-4-O-phytyl-2,3,6-trimethylhydroquinone-1-acetate (5) in 100 ml of carbon tetrachloride were cooled to about −30° C., and 0.44 ml (3.58 mmol) of boron trifluoride etherate was added dropwise. The solution was stirred at −28 to −22° C. while monitoring the course of the reaction by thin layer chromatography (TLC). After 18 minutes reaction time, when the TLC showed complete conversion of the starting material to 3-phytyl-2,5,6-trimethylhydroquinone-1-acetate (6), the reaction was quenched by the addition of 10 ml of saturated aqueous sodium bicarbonate solution. The mixture was poured into 200 ml of deionized water and 200 ml of diethyl ether. The layers were separated, the aqueous phase extracted with diethyl ether und the combined organic phases washed successively with deionized water and brine and dried over anhydrous sodium sulphate. The solution was filtered and evaporated to yield 7.1 g of a yellow oil which was chromatographed on silica gel 60 (70–230 mesh) with hexane, hexane containing 2% ethyl acetate and hexane containing 5% ethyl acetate. There were obtained 1.36 g of (RS,R,R)-α-tocopherol acetate and 4.00 g of (E,R,R)-3-phytyl-2,5,6-trimethylhydroquinone-1-acetate, $[\alpha]_D^{25}=0.10°$ (1.98% in hexane).

The invention claimed is:

1. A process for the manufacture of 3-phytyl-2,5,6-trimethylhydroquinone-1-acetate, and optionally therefrom tocopheryl acetate, which comprises either
   (a) C-alkylating 2,3,6-trimethylhydroquinone-1-acetate with isophytol or phytol in the presence of a sulphur (VI) containing catalyst of the formula $R^1SO_2OH$, wherein $R^1$ signifies hydroxy, halogen, lower alkyl, halogenated lower alkyl or aryl, in an aprotic organic solvent, or
   (b) O-alkylating 2,3,6-trimethylhydroquinone-1-acetate with a phytyl halide in a polar aprotic organic solvent in the presence of a base, and subjecting the so-obtained 4-O-phytyl-2,3,6-trimethyl hydroquinone-1-acetate to a rearrangement reaction,
   and in each case optionally submitting the so-obtained 3-phytyl-2,5,6-trimethylhydroquinone-1-acetate to a ring closure reaction to produce tocopheryl acetate.

2. A process according to claim 1 for the manufacture of 3-phytyl-2,5,6-trimethylhydroquinone-1-acetate, which comprises C-alkylating 2,3,6-trimethylhydroquinone-1-acetate with isophytol or phytol in the presence of a sulphur (VI) containing catalyst of the formula $R^1SO_2OH$, wherein $R^1$ signifies hydroxy, halogen, lower alkyl, halogenated lower alkyl or aryl, in an aprotic organic solvent.

3. A process according to claim 1 for the manufacture of 3-phytyl-2,5,6-trimethylhydroquinone-1-acetate, which comprises O-alkylating 2,3,6-trimethylhydroquinone-1-acetate with a phytyl halide in a polar aprotic organic solvent in the presence of a base, and subjecting the so-obtained 4-O-phytyl-2,3,6-trimethylhydroquinone-1-acetate to a rearrangement reaction.

4. A process for the manufacture of tocopheryl acetate according to claim 1, which comprises submitting 3-phytyl-2,5,6-trimethylhydroquinone-1-acetate or an isomer thereof to a ring closure reaction by treating said acetate with an acidic catalyst in the presence or absence of a solvent.

5. A process according to claim 1 for the manufacture of tocopheryl acetate, which comprises C-alkylating 2,3,6-trimethylhydroquinone-1-acetate with isophytol or phytol in the presence of a sulphur(VI) containing catalyst of the formula $R^1SO_2OH$, wherein $R^1$ signifies hydroxy, halogen, lower alkyl, halogenated lower alkyl or aryl, in an aprotic organic solvent, and submitting the so-obtained 3-phytyl-2,5,6-trimethylhydroquinone-1-acetate to a ring closure reaction by treating it with an acidic catalyst in the presence or absence of a solvent to produce the tocopheryl acetate.

6. A process according to claim 1 for the manufacture of tocopheryl acetate, which comprises O-alkylating 2,3,6-trimethylhydroquinone-1-acetate with a phytyl halide in a polar aprotic organic solvent in the presence of a base, subjecting the so-obtained 4-O-phytyl-2,3,6-trimethylhydroquinone-1-acetate to a rearrangement reaction, and submitting the so-obtained 3-phytyl-2,5,6-trimethylhydroquinone-1-acetate to a ring closure reaction by treating it with an acidic catalyst in the presence or absence of a solvent to produce tocopheryl acetate.

7. A process according to claim 1, wherein the sulphur (VI) containing catalyst of the formula $R^1SO_2OH$ used in the C-alkylation is selected from the group consisting of sulphuric acid, fluorosulphonic acid, methane- or ethanesulphonic acid, trifluoromethanesulphonic acid and benzene- or p-toluenesulphonic acid.

8. A process according to claim 1, wherein the aprotic organic solvent used in the C-alkylation is a polar aprotic organic solvent, or is a non-polar aprotic organic solvent, or is a biphasic solvent system containing both kinds of aprotic organic solvents.

9. A process according to claim 1, wherein the sulphur (VI) containing catalyst of the formula $R^1SO_2OH$ used in the C-alkylation is present in an amount of from about 0.01 mol. % to about 1 mol. % based on the molar amount of phytol or isophytol, whichever is employed.

10. A process according to claim 1, wherein the C-alkylation is effected at temperatures from about 20° C. to about 160° C.

11. A process according to claim 1, wherein the phytyl halide used in the O-alkylation is phytyl bromide or phytyl chloride.

12. A process according to claim 1, wherein the base used in the O-alkylation is sodium hydride.

13. A process according to claim 1, wherein the aprotic organic solvent used in the O-alkylation is a polar aprotic organic solvent.

14. A process according to claim 1, wherein the base for the O-alkylation is used in excess relative to the amount of 2,3,6-trimethylhydroquinone-1-acetate.

15. A process according to claim 1, wherein the O-alkylation is effected at temperatures from about −20° C. to about +30° C.

16. A process according to claim 1, wherein the rearrangement reaction following the O-alkylation is suitably performed in the presence of an acidic catalyst, in an aprotic organic solvent and at temperatures below about 20° C.

17. A process according to claim 16, wherein the aprotic organic solvent is an alkane; a halogenated alkane; or a mixture of these two types of aprotic organic solvents.

18. A process according to claim 16, wherein the rearrangement reaction is performed at temperatures from about −28° C. to about −23° C.

19. A process according to claim 1, wherein the ring closure is effected by treating said acetate with an acidic catalyst which is a sulphur(VI) containing catalyst of the formula $R^1SO_2OH$ wherein $R^1$ signifies hydroxy, halogen, lower alkyl, halogenated lower alkyl or aryl.

20. A process according to claim 1, wherein the ring closure is effected in a polar aprotic organic solvent.

21. A process according to claim 1, wherein the catalyst used in the ring closure is present in an amount of from about 0.01 mol. % to about 10 mol. % based on the molar amount of the 3-phytyl-2,5,6-trimethylhydroquinone-1-acetate.

22. A process according to claim 1, wherein the ring closure reaction is effected at temperatures from about 20° C. to about 160° C.

23. A process according to claim 4, wherein the 3-phytyl-2,5,6-trimethylhydroquinone-1-acetate or an isomer thereof is (Z)-4-hydroxy-2,3,6-trimethyl-5-(3,7,11,15-tetramethylhexadec-3-enyl)-phenyl acetate, (E)-4-hydroxy-2,3,6-trimethyl-5-(3,7,11,15-tetramethylhexadec-3-enyl)-phenyl acetate, or 4-hydroxy-2,3,6-trimethyl-5-[3-(4,8,12-trimethyltridecyl)-but-3-enyl]-phenyl acetate.

24. A process according to claim 8, wherein the polar aprotic organic solvent is an aliphatic or cyclic ketone; an aliphatic or cyclic ester; or a dialkyl or alkylene carbonate; and the non-polar aprotic organic solvent is an aliphatic hydrocarbon or an aromatic hydrocarbon.

25. A process according to claim 24, wherein the aliphatic or cyclic ketone is diethyl ketone, isobutyl methyl ketone, cyclopentanone, or isophorone; the aliphatic or cyclic ester is ethyl acetate, isopropyl acetate, or γ-butyrolactone; the dialkyl or alkylene carbonate is dimethyl carbonate, diethyl carbonate, ethylene carbonate, or propylene carbonate; the aliphatic hydrocarbon is hexane, heptane, or octane; and the aromatic hydrocarbon is benzene, toluene, or xylene.

26. A process according to claim 8, wherein the aprotic organic solvent used in the C-alkylation is a biphasic solvent system containing ethylene and/or propylene carbonate as the polar aprotic organic solvent and hexane, heptane, or octane as the non-polar aprotic organic solvent.

27. A process according to claim 9, wherein the sulphur (VI) containing catalyst of the formula $R^1SO_2OH$ used in the C-alkylation is present in an amount of from about 0.05 mol. % to about 0.1 mol. % based on the molar amount of phytol or isophytol, whichever is employed.

28. A process according to claim 10, wherein the C-alkylation is effected at temperatures from about 80° C. to about 150° C.

29. A process according to claim 28, wherein the C-alkylation is effected at temperatures from about 100° C. to about 127° C.

30. A process according to claim 13, wherein the polar aprotic organic solvent is selected from the group consisting of an aliphatic or cyclic ketone; an aliphatic or cyclic ester; a dialkyl or alkylene carbonate; and a dialkylformamide.

31. A process according to claim 30, wherein the aliphatic or cyclic ketone is diethyl ketone, isobutyl methyl ketone, cyclopentanone, or isophorone; the aliphatic or cyclic ester is ethyl acetate, isopropyl acetate, or γ-butyrolactone; the dialkyl or alkylene carbonate is dimethyl carbonate, diethyl carbonate, ethylene carbonate, or propylene carbonate; and the dialkylformamide is dimethylformamide or dibutylformamide.

32. A process according to claim 14, wherein the base for the O-alkylation is used in a molar excess of about 5 to about 30% relative to the amount of 2,3,6-trimethylhydroquinone-1-acetate.

33. A process according to claim 32, wherein the base for the O-alkylation is used in a molar excess of about 10 to about 20% relative to the amount of 2,3,6-trimethylhydroquinone-1-acetate.

34. A process according to claim 15, wherein the O-alkylation is effected at temperatures from about −10° C. to about +15° C.

35. A process according to claim 1, wherein the O-alkylation is effected at temperatures from about 100° C. to about 127° C.

* * * * *